US007307053B2

(12) United States Patent
Tasz et al.

(10) Patent No.: US 7,307,053 B2
(45) Date of Patent: Dec. 11, 2007

(54) COMBINATION AIR SANITIZER, SOFT SURFACE DEODORIZER/SANITIZER AND HARD SURFACE DISINFECTANT

(75) Inventors: Maciej K. Tasz, Racine, WI (US); George J. Svoboda, Whitefish Bay, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 24 days.

(21) Appl. No.: 11/313,298

(22) Filed: Dec. 20, 2005

(65) Prior Publication Data
US 2007/0142260 A1 Jun. 21, 2007

(51) Int. Cl.
C11D 1/62 (2006.01)
C11D 3/43 (2006.01)
C11D 3/06 (2006.01)

(52) U.S. Cl. ............ 510/384; 510/238; 510/255; 510/258; 510/278; 510/279; 510/342; 510/382; 510/401; 510/432; 510/467; 510/510; 510/512; 422/4; 422/5; 422/28

(58) Field of Classification Search ............ 422/4, 422/5, 28; 510/238, 255, 258, 279, 278, 510/342, 382, 384, 401, 432, 467, 510, 512
See application file for complete search history.

(56) References Cited

U.S. PATENT DOCUMENTS

| 3,160,555 A | 12/1964 | Hamill et al. |
| 3,567,118 A | 3/1971 | Shepherd et al. |
| 3,943,242 A | 3/1976 | Fogel et al. |
| 3,993,250 A | 11/1976 | Shure |
| 4,048,369 A | 9/1977 | Johnson |
| 4,054,647 A | 10/1977 | Harich et al. |
| 4,184,985 A | 1/1980 | Scheuermann et al. |
| 4,294,821 A | 10/1981 | Neumiller |
| 4,540,721 A | 9/1985 | Staller |
| 4,606,842 A | 8/1986 | Keyes et al. |
| 4,652,389 A | 3/1987 | Moll |
| 4,690,779 A | 9/1987 | Baker et al. |
| 4,740,366 A | 4/1988 | Winston et al. |
| 4,851,212 A | 7/1989 | Winston et al. |
| 4,880,557 A | 11/1989 | Ohara et al. |
| 4,883,651 A | 11/1989 | Meyer |
| 4,906,462 A | 3/1990 | Miki et al. |
| 4,934,609 A | 6/1990 | Lindauer et al. |
| 4,938,416 A | 7/1990 | Bertrand et al. |
| 5,094,761 A | 3/1992 | Trinh et al. |
| 5,102,564 A | 4/1992 | Gardlik et al. |
| 5,126,068 A | 6/1992 | Burke et al. |
| 5,167,950 A | 12/1992 | Lins |
| 5,219,890 A * | 6/1993 | Boucher ............ 514/705 |
| 5,352,437 A | 10/1994 | Nakagawa et al. |
| 5,380,707 A | 1/1995 | Barr et al. |
| 5,444,094 A | 8/1995 | Malik et al. |
| 5,496,858 A | 3/1996 | Eggensperger et al. |
| 5,578,563 A | 11/1996 | Trinh et al. |
| 5,591,395 A * | 1/1997 | Schroeder et al. ............ 422/4 |
| 5,593,670 A | 1/1997 | Trinh et al. |
| 5,663,134 A | 9/1997 | Trinh et al. |
| 5,668,097 A | 9/1997 | Trinh et al. |
| 5,670,475 A | 9/1997 | Trinh et al. |
| 5,714,137 A | 2/1998 | Trinh et al. |
| 5,783,544 A | 7/1998 | Trinh et al. |
| 5,908,854 A | 6/1999 | McCue et al. |
| 5,916,917 A | 6/1999 | Suh et al. |
| 5,929,016 A | 7/1999 | Harrison |
| 5,935,554 A | 8/1999 | Tomlinson |
| 5,939,060 A | 8/1999 | Trinh et al. |
| 5,939,374 A | 8/1999 | Richter et al. |
| 5,942,217 A | 8/1999 | Woo et al. |
| 5,955,093 A | 9/1999 | Woo et al. |
| 5,955,414 A | 9/1999 | Brown et al. |
| 5,968,404 A | 10/1999 | Trinh et al. |
| 5,985,819 A | 11/1999 | Lu et al. |
| 5,997,759 A | 12/1999 | Trinh et al. |
| 6,001,343 A | 12/1999 | Trinh et al. |
| 6,033,679 A | 3/2000 | Woo et al. |
| 6,077,318 A | 6/2000 | Trinh et al. |
| 6,080,387 A | 6/2000 | Zhou et al. |
| 6,117,440 A | 9/2000 | Suh et al. |
| 6,146,621 A | 11/2000 | Trinh et al. |
| 6,177,070 B1 | 1/2001 | Lynch |
| 6,248,135 B1 | 6/2001 | Trinh et al. |
| 6,268,327 B1 | 7/2001 | Lu et al. |

(Continued)

FOREIGN PATENT DOCUMENTS

DE 1617148 7/1950

(Continued)

*Primary Examiner*—Charles Boyer

(57) ABSTRACT

An improved combination air sanitizer, soft surface sanitizer, soft surface deodorizer and hard surface disinfectant is disclosed. The preferred active ingredient for the air sanitization and soft surface odor treatment functions is triethylene glycol (TEG). The preferred active ingredient for soft surface sanitization and hard surface disinfection functions is a mixture of various alkyl dimethyl benzyl ammonium saccharinates. The formulation may be provided in an aerosol spray form and is useful for sanitizing and removing bacteria and malodorant molecules from the air as well as disinfecting hard surfaces. A unique combination of corrosion inhibitors is disclosed for convention steel or tin-plated steel cans. A single produce can be used as an air sanitizer/air freshener, a soft surface sanitizer, a soft-surface odor remover/reducer and, a hard surface disinfectant.

24 Claims, 1 Drawing Sheet

U.S. PATENT DOCUMENTS

| | | |
|---|---|---|
| 6,284,231 B1 | 9/2001 | Trinh et al. |
| 6,395,236 B1 | 5/2002 | Stewart |
| 6,395,397 B2 | 5/2002 | Hong et al. |
| 6,428,801 B1 | 8/2002 | Suh et al. |
| 6,451,065 B2 | 9/2002 | Trinh et al. |
| 6,454,876 B1 | 9/2002 | Ochomogo et al. |
| 6,471,974 B1 | 10/2002 | Rees et al. |
| 6,482,392 B1 | 11/2002 | Zhou et al. |
| 6,528,472 B2 | 3/2003 | Charaf et al. |
| 6,559,189 B2 | 5/2003 | Baker, Jr. et al. |
| 6,767,507 B1 | 7/2004 | Woo et al. |
| 6,794,346 B2 | 9/2004 | Wick et al. |
| 6,833,342 B2 | 12/2004 | Woo et al. |
| 6,867,174 B2 | 3/2005 | Ramirez, Jr. et al. |
| 6,943,140 B2 | 9/2005 | Ashton et al. |
| 7,030,078 B2 | 4/2006 | Cheung et al. |
| 2003/0005522 A1 | 1/2003 | Trinh et al. |
| 2003/0073602 A1 | 4/2003 | Ramirez, Jr. et al. |
| 2003/0108703 A1 | 6/2003 | Lang |
| 2003/0114342 A1 | 6/2003 | Hall |
| 2003/0145965 A1 | 8/2003 | Anderson et al. |
| 2003/0162678 A1 | 8/2003 | Ashton et al. |
| 2003/0191034 A1 | 10/2003 | Woo et al. |
| 2004/0213750 A1 | 10/2004 | Bennett et al. |
| 2005/0003990 A1 | 1/2005 | Smith et al. |
| 2005/0089540 A1 | 4/2005 | Uchiyama et al. |
| 2005/0196374 A1 | 9/2005 | Ueda |
| 2005/0202991 A1 | 9/2005 | De Dominicis et al. |
| 2005/0227897 A1 | 10/2005 | Nelson et al. |
| 2006/0228250 A1 | 10/2006 | Brown et al. |

FOREIGN PATENT DOCUMENTS

| | | |
|---|---|---|
| DE | 36 39 635 | 6/1988 |
| EP | 0928829 | 4/1999 |
| EP | 0 934 742 | 1/2002 |
| EP | 1 239 731 | 9/2002 |
| EP | 1 277 403 | 1/2003 |
| EP | 1 454 638 | 9/2004 |
| ES | 2 168 054 | 5/2002 |
| WO | WO 96/17518 | 6/1996 |
| WO | WO 97/00934 | 1/1997 |
| WO | WO 99/60085 | 11/1999 |
| WO | WO 00/12662 | 3/2000 |
| WO | WO 00/13507 | 3/2000 |
| WO | WO 00/68502 | 11/2000 |
| WO | WO 2005/089100 | 9/2005 |
| WO | PCT-WO2006/023858 A1 | 3/2006 |
| WO | WO 2007/052016 | 5/2007 |

* cited by examiner

COMBINATION AIR SANITIZER, SOFT SURFACE DEODORIZER/SANITIZER AND HARD SURFACE DISINFECTANT

BACKGROUND

1. Technical Field

A combination air sanitizer, soft surface deodorizer/sanitizer and hard surface disinfectant is disclosed which provides the novel combination of triethylene glycol as an air sanitizer and soft surface deodorizer and an alkyl dimethyl benzyl ammonium saccharinate as a soft surface sanitizer and hard surface disinfectant. A method for sanitizing air, sanitizing soft surfaces, treating odors in soft surfaces and disinfecting hard surfaces with a single formulation is also disclosed.

2. Description of the Related Art

Aerosol spray air sanitizers are known. However, the active ingredients in currently-available aerosol air sanitizers vary. One family of products relies upon glycols, the most popular of which is triethylene glycol, the active ingredient in the OUST® family of products sold by S.C. Johnson & Son, Inc., the assignee of this application. Triethylene glycol (TEG) is known to kill certain airborne bacteria. TEG is also safe for use in aerosol sprays. Ethanol is typically used as co-solvent with water to increase volatility.

The use of sanitizing and disinfecting herein is consistent with Environmental Protection Agency Disinfectant Technical Science Section (DIS-TSS) nos. 01, 08, 11 and 13 (http://www.epa.gov/oppad001/sciencepolicy.htm). Briefly, for hard surfaces, the term "disinfecting" refers to a complete kill of all bacteria on a test surface while the term "sanitizing" refers to a less than complete kill of the bacteria on a test surface. Disinfecting is not associated with air treatment or soft surface treatment products; instead, the term sanitizing is used and the EPA separate requirements for air (DIS-TSS 11) and certain soft surfaces like carpeting (DIS-TSS 08).

Soft surface deodorizers are also known. The term "soft surfaces" herein will be used to refer to describe carpeting, upholstery and other fabrics that are porous as opposed to hard, non-porous surfaces like kitchen countertops. One family of soft surface deodorizers sold under the FEBREZE® trademark rely upon the use of ethanol in combination with cyclodextrins, a material derived from corn. In addition to being marketed for use as deodorizers for fabrics, upholstery and carpeting, these cyclodextrin products have also been marketed for use as air fresheners or deodorizers.

Instead of killing bacteria like TEG, cyclodextrins have a toroidal structure with a hydrophilic exterior and a hydrophobic interior. The hydrophobic interior gives cyclodextrins the unique ability to entrap malodorous compounds within the toroidal structure, thereby leaving the malodorous compounds undetectable by the human sense of smell.

Another approach to treating odors in soft surfaces utilizes water soluble/dispersible polymers as taught in U.S. Pat. No. 6,454,876. In contrast to cyclodextrins, which trap or cage the odor-causing molecule within the cyclodextrin toroid as discussed above, the water soluble/dispersible polymers of the '876 patent entraps the odor-causing molecule by forming a film that blankets the odor-causing molecule. The film is formed as the solvent or carrier evaporates. The residual polymer film provides a barrier to contain the odor-causing material in the soft surface thereby preventing its release to the ambient environment and detection by the consumer's sense of smell.

Both the cyclodextrin and film-forming polymer products leave a residue after the solvent or carrier evaporates. Further, neither cyclodextrins nor film-forming polymers have any anti-microbial properties.

Currently available disinfectant sprays are primarily directed toward sanitization or disinfection of hard (i.e., non-porous) surfaces. Alkyl dimethyl benzyl ammonium saccharinate in combination with ethanol is a popular family of compounds for disinfecting hard surfaces. Other known disinfectants include n-alkyl dimethyl benzyl ammonium chlorides and n-alkyl dimethyl ethylbenzyl ammonium chlorides. These compounds are not intended to remove airborne bacteria or treat soft surface odors, but instead are intended to disinfect hard surfaces.

Other antimicrobials as set forth in Block, S., *Disinfection, Sterilization and Preservation*, Lea & Febiger (1983) include chlorine and chlorine compounds, iodine and iodine compounds, phenolic compounds, alcohols, hydrogen peroxide and other oxidant disinfectants, chlorhexidine, nitrogen compounds, surface-active agents such as quaternary ammonium compounds, acid-anionic compounds, amphoteric compounds, mercurials—inorganic and organic, silver and silver-containing compounds, heavy metals other than mercury and silver. In the class of quaternary ammonium salts, Block cites monoalkyltrimethyl ammonium salts, monoalkyldimethylbenzyl ammonium salts, dialkyldimethyl ammonium salts, and heteroaromatic ammonium salts. In addition, polysubstituted quaternary ammonium salts, bis-quaternary ammonium salts and polymeric quaternary ammonium salts are known to have disinfectant properties.

Therefore, the TEG-containing products are intended primarily to sanitize air and the disinfectant-containing products (e.g., alkyl dimethyl benzyl ammonium saccharinates) are intended primarily to disinfect hard surfaces. The cyclodextrin-containing products are intended to freshen air and treat odors in soft surfaces. The film forming products treat odors in soft surfaces only.

Currently, no single aerosol or pump spray formulation is intended to sanitize air, treat airborne odors, treat odors in soft surfaces, sanitize soft surfaces, and disinfect hard surfaces. While currently available products may be used for both purposes, their effectiveness is limited to a single purpose. Specifically, the glycol containing aerosol sprays are excellent at deodorizing and sanitizing air but cannot disinfect hard surfaces. The cyclodextrin containing sprays are effective by removing odors in soft surfaces such as upholstery, carpeting and clothing, but are not particularly useful for removing odors from air. Because cyclodextrins and film-forming polymers cage, entrap or blanket the malodorous compounds, they are typically not used with hard surface disinfectants as they are intended to remain in the soft surface indefinitely or until the surface is cleaned or washed. In contrast, the disinfectant-containing products are useful on hard surfaces but are not effective at sanitizing or removing odors from air or soft surfaces.

Further, consumers tend to confuse the purposes of the above-described products. Specifically, the consumer may believe that a disinfectant spray intended for hard surfaces is actually effective at removing odors from the air or sanitizing the air when it is not. The consumer may therefore use a disinfectant aerosol spray in the air with limited or adverse results. Further, a consumer may use an air sanitizer, such as one containing glycols, on hard surfaces and believe that he or she is actually disinfecting those surfaces when, in fact, the disinfectant properties of an air sanitizer are very limited.

Thus, the use of an air sanitizer and air freshener on a hard surface, such as a food preparation surface, may leave the consumer with the impression that the food preparation surface has been sanitized, when it has not.

Therefore, a combination air sanitizer/soft surface deodorizer/soft surface sanitizer/hard surface disinfectant is not currently available and is needed. By combining multiple functions—air freshening/sanitizing with soft surface freshening/sanitizing with hard surface disinfecting, the consumer would be able to purchase one product for three important tasks thereby saving the consumer money and conserving home storage space.

SUMMARY OF THE DISCLOSURE

An improved formulation for sanitizing air by killing airborne bacteria, deodorizing and sanitizing soft surfaces and disinfecting hard surfaces is provided. The formulation may be provided in aerosol spray form or a spray pump form.

In a refinement, the active ingredient for air sanitization and soft surface odor treatment is triethylene glycol (TEG) and an active ingredient for both soft surface sanitization and hard surface disinfecting is an alkyl dimethyl benzyl ammonium saccharinate. However, other glycols such as dipropylene, and/or propylene glycols may be used instead of or in conjunction with TEG. Other "quats" or other quaternary ammonium salts may be used instead of or in addition to the alkyl dimethyl benzyl ammonium saccharinate.

As the formulation is preferably delivered as an aerosol spray and is therefore provided in a metal canister with a spray nozzle, the formulation also preferably includes at least one corrosion inhibitor. A combination of mono- and di-potassium phosphates are provided. Still more preferably, the combination of mono- and di-potassium phosphates is supplemented by potassium nitrite. Of course, non-aerosol sprays would not require corrosion inhibition as they are provided in plastic spray pump containers.

As an alternative, a combination of mono- and di-sodium phosphates can be used in lieu or in combination with the potassium phosphates. Still more preferably, the combination of mono- and di-sodium phosphates can be supplemented by sodium or potassium nitrite. In short, potassium or sodium phosphates or mixtures of potassium and sodium phosphates and nitrites can be used for corrosion inhibition.

As still another alternative, ammonium phosphates and/or ammonium nitrite may be used or combined with the inhibitors discussed above. However, ammonium nitrite is explosive and therefore presents handling problems. Tri-potassium and tri-sodium phosphates could also be used and neutralized to an acceptable pH with an acid such as phosphoric acid. This strategy would mimic the action of the mono- and di-potassium/sodium/ammonium phosphates as discussed above. As another alternative, corrosion inhibition may be provided by borax ($Na_2B_4O_7.H_2O$) alone or in combination sodium nitrite or with one more of the other inhibitors discussed above.

In another refinement, a short chain monohydric alcohol is used with water as a co-solvent. Isopropanol, butanol, ethanol and propanol can be used.

In yet another refinement, the aerosol spray includes at least one hydrocarbon propellant. In yet another refinement, the formulation also comprises fragrance.

Regarding the active hard surface disinfecting ingredient, the alkyl dimethyl benzyl ammonium saccharinate may be selected from the group consisting of $C_{14}$, $C_{12}$ and $C_{16}$ dimethyl benzyl ammonium saccharinates. In a further refinement, the alkyl dimethyl benzyl ammonium saccharinate comprises a mixture of $C_{14}$, $C_{12}$ and $C_{16}$ alkyl dimethyl benzyl ammonium saccharinates. In still a further refinement of this concept, the mixture of $C_{14}$, $C_{12}$ and $C_{16}$ alkyl dimethyl benzyl ammonium saccharinates consists essentially of about 50 wt % $C_{14}$ alkyl dimethyl benzyl ammonium saccharinate, about 40 wt % $C_{1-2}$ alkyl dimethyl benzyl ammonium saccharinate and about 10 wt % $C_{1-6}$ alkyl dimethyl benzyl ammonium saccharinate.

Other suitable disinfectants include: a mixture of dialkyldimethylammonium chloride and n-alkyldimethylbenzylammonium chloride; a mixture of n-alkyldimethylbenzyl chloride and n-alkyldimethyl(ethylbenzyl)chloride; a mixture of didecyldimethylammonium carbonate and bicarbonate; and an n-alkyldimethylbenzylammonium chloride solution in water.

Regarding the soft surface odor treatment and sanitization properties, it will be noted first that the quaternary ammonium salt, i.e., the alkyl dimethyl benzyl ammonium saccharinate acts as a sanitizer in a soft surface environment. Odor treatment is achieved through the TEG. Specifically, without being bound to any theory, it is believed that agglomerations of TEG, solvent(s), and fragrance can form in the soft surface. When odor-causing materials engage these agglomerations, the odor-causing materials are dissolved into the agglomeration thereby reducing the partial vapor pressure of the odor-causing material. As the TEG remains in a liquid form, no dried residue is apparent or visible.

In summary, a disclosed formulation for sanitizing air by removing or killing airborne bacteria in air, for sanitizing soft surfaces, for treating odors in soft surfaces and for disinfecting hard surfaces, comprises triethylene glycol, at least one alkyl dimethyl benzyl ammonium saccharinate, water and a short chain monohydric alcohol.

A preferred aerosol formulation comprises from about 3 to about 10 wt % triethylene glycol, from about 0.05 to about 1 wt % of at least one alkyl dimethyl benzyl ammonium saccharinate, from about 10 to about 40 wt % water, from about 30 to about 70 wt % of an alcohol, propellant, fragrance and at least one corrosion inhibitor.

A preferred spray pump formulation comprises from about 3 to about 10 wt % triethylene glycol, from about 0.05 to about 1 wt % of at least one alkyl dimethyl benzyl ammonium saccharinate, from about 60 to about 80 wt % water, from about 35 to about 70 wt % of an alcohol, propellant, fragrance and the balance, water.

A method for sanitizing air, treating odors in soft a surface, sanitizing the soft surface and disinfecting a hard surface comprises providing either the aerosol or spray formulation described above, spraying the formulation in the air, spraying the formulation on the soft surface and spraying the formulation on the hard surface.

Other advantages and features of the disclosed embodiments and methods will be described in the following detailed description of the presently preferred embodiments.

BRIEF DESCRIPTION OF THE DRAWINGS

One embodiment of an aerosol product packaged in a can not susceptible to corrosion and therefore not in need of corrosion inhibitors in the formulation is shown in FIG. 1 which is a front sectional view of an aerosol can made in accordance with one embodiment.

DETAILED DESCRIPTION OF THE PRESENTLY PREFERRED EMBODIMENTS

Figure 1:
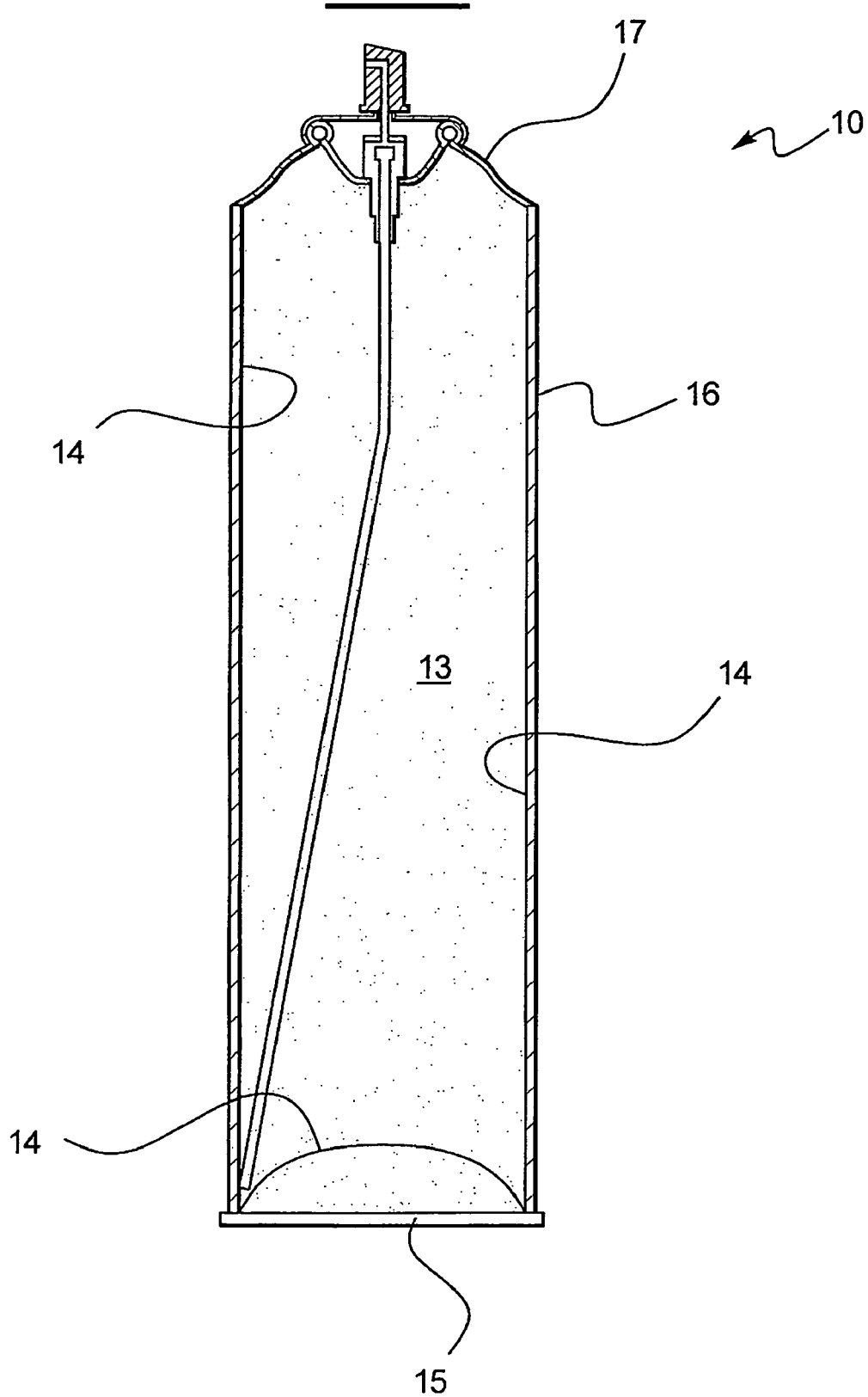

Preferred combination air sanitizer/soft surface sanitizer/soft surface odor control/hard surface disinfectant aerosol spray formulations include deionized water, ethanol, triethylene glycol (TEG), ONYXIDE 3300™ ((20 wt % solution) alkyl (50% $C_{14}$, 40% $C_{12}$, 10% $C_{16}$) dimethyl benzyl ammonium saccharinate), mono-potassium phosphate, di-potassium phosphate, potassium nitrite, fragrance and hydrocarbon propellant. Non-aerosol formulations do not include the propellant, the phosphates or the nitrite as shown in Example 5.

The combination of the potassium phosphates and potassium nitrite might be varied. The potassium nitrite may be eliminated (compare Examples 1 and 2). One of the potassium phosphates may be eliminated. Sodium phosphates and nitrites may be substituted for the potassium phosphates and nitrites as shown below in Examples 3 and 4 and mixtures of potassium and sodium corrosion inhibitors may be employed. All three of these ingredients are used as corrosion inhibitors. As shown in Example 7, sodium benzoate and triethanolamine may also be used for corrosion inhibition alone, together or with one or more of the potassium or sodium inhibitors discussed herein.

Ethanol is a preferred co-solvent and enhances the solubility of the quaternary ammonium salt and the fragrances. Other short chain, low molecular weight, mono-hydric alcohols can be substituted for or combined with the ethanol. Suitable alcohols include, but are not limited to propanol, isopropanol (see Examples 6 and 8) and butanol.

EXAMPLE 1

| wt % | Description | Chemical Name/Trade Name |
|---|---|---|
| 35.65% | solvent | deionized water |
| 37.56% | solvent (solution for fragrance and quaternary) | ethanol |
| 6.12% | air sanitizer/soft surface odor treatment | triethylene glycol (TEG) |
| 0.20% | quaternary (hard surface disinfectant) | ONYXIDE 3300 ™, alkyl (50% $C_{14}$, 40% $C_{12}$, 10% $C_{16}$) dimethyl benzyl ammonium saccharinate |
| 0.02% | corrosion inhibitor/buffer | $KH_2PO_4$, mono-potassium phosphate |
| 0.18% | corrosion inhibitor/buffer | $K_2HPO_4$, di-potassium phosphate |
| 0.12% | corrosion inhibitor | $KNO_2$, potassium nitrite |
| 0.15% | mixture of fragrances | TAKASAGO ™ RK 1428; IFF 1401 HBA; Firmenich SJ 446138 |
| 20.00% | hydrocarbon propellant | A-57 (propane/isobutene); B-52 (butane/propane/isobutene) |
| 100.00% | | |

EXAMPLE 2

| wt % | Description | Chemical Name/Trade Name |
|---|---|---|
| 35.65% | solvent | deionized water |
| 37.68% | solvent (solution for fragrance and quaternary) | ethanol |
| 6.12% | air sanitizer | triethylene glycol (TEG) |
| 0.20% | quaternary (hard surface disinfectant) | ONYXIDE 3300 ™, alkyl (50% $C_{14}$, 40% $C_{12}$, 10% $C_{16}$) dimethyl benzyl ammonium saccharinate |
| 0.02% | corrosion inhibitor/buffer | $KH_2PO_4$, mono-potassium phosphate |
| 0.18% | corrosion inhibitor/buffer | $K_2HPO_4$, di-potassium phosphate |
| 0.15% | mixture of fragrances | TAKASAGO ™ RK 1428; IFF 1401 HBA; Firmenich SJ 446138 |
| 20.00% | hydrocarbon propellant | A-57 (propane/isobutene); B-52 (butane/propane/isobutene) |
| 100.00% | | |

EXAMPLE 3

| Wt % | Description | Chemical Name/Trade Name |
|---|---|---|
| 35.65% | solvent | deionized water |
| 37.68% | solvent (solution for fragrance and quaternary) | ethanol |
| 6.12% | air sanitizer | triethylene glycol (TEG) |
| 0.20% | quaternary (hard surface disinfectant) | ONYXIDE 3300 ™, alkyl (50% $C_{14}$, 40% $C_{12}$, 10% $C_{16}$) dimethyl benzyl ammonium saccharinate |
| 0.02% | corrosion inhibitor/buffer | $NaH_2PO_4$, mono-sodium phosphate |
| 0.18% | corrosion inhibitor/buffer | $Na_2HPO_4$, di-sodium phosphate |
| 0.15% | mixture of fragrances | TAKASAGO ™ RK 1428; IFF 1401 HBA; Firmenich SJ 446138 |
| 20.00% | hydrocarbon propellant | A-57 (propane/isobutene); B-52 (butane/propane/isobutene) |
| 100.00% | | |

EXAMPLE 4

| wt % | Description | Chemical Name/Trade Name |
|---|---|---|
| 35.65% | solvent | deionized water |
| 37.56% | solvent (solution for fragrance and quaternary) | Ethanol |
| 6.12% | air sanitizer/soft surface odor treatment | triethylene glycol (TEG) |
| 0.20% | quaternary (hard surface disinfectant) | ONYXIDE 3300 ™ alkyl (50% $C_{14}$, 40% $C_{12}$, 10% $C_{16}$) dimethyl benzyl ammonium saccharinate |
| 0.02% | corrosion inhibitor/buffer | $NaH_2PO_4$, mono-sodium phosphate |
| 0.18% | corrosion inhibitor/buffer | $Na_2HPO_4$, di-sodium phosphate |
| 0.12% | corrosion inhibitor | $NaNO_2$, sodium nitrite |

-continued

| wt % | Description | Chemical Name/Trade Name |
|---|---|---|
| 0.15% | mixture of fragrances | TAKASAGO ™ RK 1428; IFF 1401 HBA; Firmenich SJ 446138 |
| 20.00% | hydrocarbon propellant | A-57 (propane/isobutene); B-52 (butane/propane/isobutene) |
| 100.00% | | |

EXAMPLE 5

| wt % | Description | Chemical Name/Trade Name |
|---|---|---|
| 55.97% | solvent | deionized water |
| 37.56% | solvent (solution for fragrance and quaternary) | ethanol |
| 6.12% | air sanitizer/soft surface odor treatment | triethylene glycol (TEG) |
| 0.20% | quaternary (hard surface disinfectant) | ONYXIDE 3300 ™, alkyl (50% $C_{14}$, 40% $C_{12}$, 10% $C_{16}$) dimethyl benzyl ammonium saccharinate |
| 0.15% | mixture of fragrances | TAKASAGO ™ RK 1428; IFF 1401 HBA; Firmenich SJ 446138 |
| 100.00% | | |

EXAMPLE 6

| wt % | Description | Chemical Name/Trade Name |
|---|---|---|
| 55.17% | solvent | deionized water |
| 37.56% | solvent (solution for fragrance and quaternary) | isopropanol |
| 6.12% | air sanitizer/soft surface odor treatment | triethylene glycol (TEG) |
| 1.00% | quaternary (hard surface disinfectant) | ONYXIDE 3300 ™, alkyl (50% $C_{14}$, 40% $C_{12}$, 10% $C_{16}$) dimethyl benzyl ammonium saccharinate |
| 0.15% | mixture of fragrances | TAKASAGO ™ RK 1428; IFF 1401 HBA; Firmenich SJ 446138 |
| 100.00% | | |

EXAMPLE 7

| wt % | Description | Chemical Name/Trade Name |
|---|---|---|
| 13.53% | solvent | deionized water |
| 63.43% | solvent (solution for fragrance and quaternary) | ethanol |
| 6.00% | air sanitizer/soft surface odor treatment | triethylene glycol (TEG) |

-continued

| wt % | Description | Chemical Name/Trade Name |
|---|---|---|
| 0.09% | Quaternary (hard surface disinfectant) | ONYXIDE 3300 ™, alkyl (50% $C_{14}$, 40% $C_{12}$, 10% $C_{16}$) dimethyl benzyl ammonium saccharinate |
| 0.2% | corrosion inhibitor | $Na_2B_4O_7 \cdot H_2O$, borax |
| 0.1% | corrosion inhibitor | $NaNO_2$, sodium nitrite |
| 0.15% | mixture of fragrances | fragrance oils |
| 16.5% | hydrocarbon propellant | |
| 100.00% | | |

EXAMPLE 8

| wt % | Description | Chemical Name/Trade Name |
|---|---|---|
| 25.00% | solvent | deionized water |
| 47.58% | solvent (solution for fragrance and quaternary) | isopropanol |
| 0.8% | solvent | ethanol |
| 6.12% | air sanitizer/soft surface odor treatment | triethylene glycol (TEG) |
| 0.20% | quaternary (hard surface disinfectant) | ONYXIDE 3300 ™, alkyl (50% $C_{14}$, 40% $C_{12}$, 10% $C_{16}$) dimethyl benzyl ammonium saccharinate |
| 0.1% | corrosion inhibitor | triethanolamine $(HOCH_2CH_2)_3N$ |
| 0.2% | corrosion inhibitor | sodium benzoate, $C_7H_5O_2Na$ |
| 20.00% | hydrocarbon propellant | |
| 100.00% | | |

EXAMPLE 9

| wt % | Description | Chemical Name/Trade Name |
|---|---|---|
| 13.53% | solvent | deionized water |
| 63.46% | solvent (solution for fragrance and quaternary) | ethanol |
| 6.00% | air sanitizer/soft surface odor treatment | triethylene glycol (TEG) |
| 0.09% | quaternary (hard surface disinfectant) | ONYXIDE 3300 ™, alkyl (50% $C_{14}$, 40% $C_{12}$, 10% $C_{16}$) dimethyl benzyl ammonium saccharinate |
| 0.1% | corrosion inhibitor | triethanolamine $(HOCH_2CH_2)_3N$ |
| 0.2% | corrosion inhibitor | sodium benzoate, $C_7H_5O_2Na$ |
| 0.15% | mixture of fragrances | TAKASAGO ™ RK 1428; IFF 1401 HBA; Firmenich SJ 446138 |
| 16.47% | hydrocarbon propellant | A-57 (propane/isobutene); B-52 (butane/propane/isobutene) |
| 100.00% | | |

EXAMPLE 10

| wt % | Description | Chemical Name/Trade Name |
|---|---|---|
| 10.00% | solvent | deionized water |
| 63.55% | solvent (solution for fragrance and quaternary) | ethanol |
| 6.00% | air sanitizer/soft surface odor treatment | triethylene glycol (TEG) |
| 0.30% | quaternary (hard surface disinfectant) | BTC 2125M, mixture of n-alkyldimethylbenzyl chloride and n-alkyldimethyl(ethylbenzyl) chloride |
| 0.15% | mixture of fragrances | TAKASAGO ™ RK 1428; IFF 1401 HBA; Firmenich SJ 446138 |
| 20.00% | hydrocarbon propellant | A-57 (propane/isobutene); B-52 (butane/propane/isobutene) |
| 100.00% | | |

Water and the short chain alcohol serve as co-solvents. The use of ethanol, isopropanol, propanol or butanol facilitates the solubization of the disinfectant/soft surface sanitizer, i.e. the alkyl dimethyl benzyl ammonium saccharinates, as well as the fragrance, which is typically a mixture of fragrance oils. The alcohol content can range from 25 to 50 wt %, more preferably from about 35 to about 45 wt %. The water content is preferably in the range of the alcohol content for an aerosol embodiment and therefore may also range from about 25 to about 50 wt %, or preferably from about 30 to about 40 wt %. Deionized water is preferred for both aerosol and spray pump formulations.

The air sanitizer/soft surface odor reducer is preferably TEG. The TEG content may range from about 3 to about 10 wt %, more preferably from about 4 to about 8 wt %. The structure of TEG is presented below:

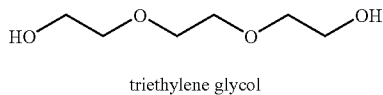

triethylene glycol

TEG is a straight chain glycol and, while a liquid at room temperature, an be utilized effectively in an aerosol or pump spray. TEG has been found to be capable of killing airborne bacteria thereby destroying odors and health risks associated therewith.

The use of TEG for odor control is extended to odors embedded in soft surfaces such as carpeting, upholstery, drapes, clothing, bedding, etc. When the composition is applied, a layer or an agglomeration is formed within the soft surface substrate in close proximity to the malodor sources. When the odor-causing molecules come into contact with the agglomeration, they dissolve in the agglomeration and their effective vapor pressure is suppressed. Many malodorous components (thiols, amines, acids, sulfites, etc.), have a very low air/solvent partition coefficients (Henry's constant), which confirms the broad-spectrum odor suppression capability of TEG. In summary, the malodorous components have a greater affinity for TEG agglomeration than air thereby reducing the vapor pressure and perception by the human sense of smell.

Glycols, in generally are reactive with many organic compounds. Triethylene glycol is prepared commercially by oxidation of ethylene at high temperatures in the presence of silver oxide to yield ethylene oxide. The ethylene oxide is then hydrated to yield mono- di- tri- and tetra-ethylene glycols. TEG is a colorless, odorless, non-volatile and hygroscopic liquid. Its two hydroxyl groups and two ether linkages contribute to its high solubility and water, hygroscopicity, solvent properties and reactivity with numerous organic, odor-causing compounds. TEG is substantially less toxic than diethylene glycol (DEG).

In addition to TEG, dipropylene glycol and/or propylene glycol may be used instead of or in conjunction with TEG.

The structure of an alkyl dimethyl benzyl ammonium saccharinate is presented below:

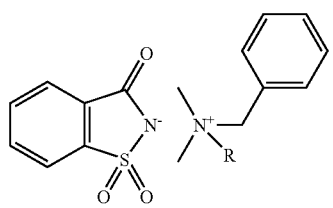

dimethyl benzyl ammonium saccharinate wherein R represents the alkyl group of alkyl dimethyl benzyl ammonium saccharinate:

A convenient source for such a quaternary ammonium compound is ONYXIDE™ 3300, sold by the Stepan Company, 22 Frontage Road, Northfield, Ill. 60093 (www.stepan.com). A particular preferred formulation includes a mixture of three variations of the alkyl group: 50 wt % $C_{14}$, 40 wt % $C_{12}$ and 10 wt % $C_{16}$. Of course, these percentages can vary and still fall within the spirit and scope of this disclosure. The disclosed alkyl dimethyl benzyl ammonium saccharinate mixture is an effective algaecide and microbiocide. The above described alkyl dimethyl benzyl ammonium saccharinate mixture is an effective quaternary germicide.

Optionally, polymeric quaternary ammonium salts based on the above structures are also useful. Further, other quaternary ammonium salts such as alkyl dimethyl benzyl ammonium chlorides may be used.

Other suitable disinfectants include: a mixture of dialkyldimethylammonium chloride and n-alkyldimethylbenzylammonium chloride sold under the tradename BARDAC™ 205M by Lonza (www.lonza.com); a mixture of n-alkyldimethylbenzyl chloride and n-alkyldimethyl(ethylbenzyl)chloride sold under the tradename BTC 2125M by Stepan (www.stepan.com); a mixture of didecyldimethylammonium carbonate and bicarbonate sold under the tradename CARBOQUAT™ by Lonza; and an n-alkyldimethylbenzylammonium chloride solution in water sold under the tradename FMB-451-5, also by Lonza.

One or more corrosion inhibitors are utilized to prevent corrosion to the aerosol can. Di-potassium phosphate ($K_2HPO_4$) is useful as both a corrosion inhibitor and a buffer. Di-potassium phosphate may be used alone or in combination with mono-potassium phosphate ($KH_2PO_4$). Di-sodium phosphate ($Na_2HPO_4$) is also useful as both a corrosion inhibitor and a buffer and may be substituted for the di-potassium phosphate. Mono-sodium phosphate ($NaH_2PO_4$) may also be used instead of or in addition to mono-potassium phosphate. The combination of di alone or di and mono-potassium and/or sodium phosphates has been found to be enhanced by the presence of another corrosion inhibitor in the form of potassium nitrite (KNO$_2$) and/or sodium nitrite (NaNO$_2$). Accordingly, the presence of di-potassium phosphate or di-sodium phosphate may range from 01. to 1.0 wt %, more preferably between 0.15 and 0.25 wt %. A suitable pH range for these salts is from about 7 to about 11, with a preferred range from about 8 to about 10.

The amount of di-potassium phosphate or di-sodium phosphate may be reduced if a small amount of mono-potassium phosphate and/or mono-sodium phosphate is utilized as shown above in Examples 1 and 4. If used, the mono-potassium phosphate and/or mono-sodium phosphate need only be present in small amounts, but their presence may range from about 0.01 to about 1.0 wt %, more preferably around 0.02 wt %. If utilized, the potassium nitrite can be present in amount ranging from about 0.01 to about 1.0 wt %, more preferably from about 0.07 to about 0.15 wt %. Further, to achieve the same objectives, the inhibitor may also be in situ with potassium hydroxide and phosphoric acid or with sodium hydroxide and phosphoric acid. The mono-potassium/sodium phosphates may be added in amounts exceeding that of the di-potassium/sodium phosphates to create buffer systems ranging from acidic to alkaline pHs ranging from about 5 to about 10, preferably from about 7 to about 9.

Also, ammonium phosphates and/or ammonium nitrite may be used or combined with the corrosion inhibitors discussed above. However, ammonium nitrite is explosive and therefore presents handling problems. Tri-potassium and tri-sodium phosphates could also be used and neutralized to an acceptable pH with an acid such as phosphoric acid. Triethanolamine with sodium benzoate or with one or more the other inhibitors discussed above is a less preferred alternative for corrosion inhibition. As another alternative, corrosion inhibition may be provided by borax (Na$_2$B$_4$O$_7$.H$_2$O) alone or in combination with sodium nitrite or with one more of the other inhibitors discussed above.

Other suitable corrosion inhibitors include MONACOR BE, AMP-95, triethanolamine/sodium benzoate, triethanolamine/sodium nitirite, a combination of 2-amino-2-methyl-1-propanol and 95% sodium benzoate, borax (5M) alone or in combination with sodium nitrite, HOSTACOR 2732, SANDOCORIN 8160, ELFUGIN AKT Liquid 300, tris (hydroxymethyl)aminomethane, or combinations thereof.

For the hydrocarbon propellant, certain mixtures of propane and/or isobutene and/or butane have been found to be effective. Various other propellant combinations may be utilized. While surface disinfectants should have large particle sizes and low pressure propellants to wet the surface and minimize bounce off of the formula, air sanitizers should deliver relatively small particles or droplets to promote evaporation of the TEG and minimize fall-out, which is typically achieved with high pressure propellants. High pressure propellants also enable faster and better distribution of the formula throughout the air space. Further, quaternary-based surface disinfectants must contain certain amounts of water for the quaternary to be active. However, water contributes to bigger particle or droplet sizes, which are not appropriate for air sanitizers. To satisfy there competing criteria, combinations of propane and isobutane (A series) or propane, isobutane and n-butane (B-series) are utilized. The numbers 57 and 52 in the above examples refer to equilibrium gas pressure over liquid (in psi) at 70° F.

FIG. 1 illustrates a three-piece aerosol can or vessel 10 for a product that does not include a corrosion inhibitor. The product does not need a corrosion inhibitor because the can 10 is either (1) fabricated from aluminum or (2) is fabricated from steel or tin-coated steel that has in interior 13 coated with a protective polymer or plastic layer 14. As shown, the can 10 is of a three-piece construction with a bottom 15, a body portion 16 and a top portion 17. It will be noted that aluminum aerosol cans typically have a one-piece construction and that two-piece steel or tin-coated steel cans with a bottom 15 and an extruded body/top portion 16, 17 are available and both fall within the scope of this disclosure. Those skilled in the art will know which readily available polymers can serve as protective coating. Certain polyethylenes, polypropylenes and polyethylenetetrafluorides are but a few examples. Both the aluminum can and protective coating alternatives avoid the need for corrosion inhibition agents, but with a significant an increase in packaging costs.

While only certain embodiments have been set forth, alternative embodiments and various modifications will be apparent from the above description to those skilled in the art. These and other alternatives are considered equivalents and within the spirit and scope of this disclosure and the appended claims.

What is claimed:

1. A formulation for sanitizing air, sanitizing soft surfaces, treating odors embedded in soft surfaces and disinfecting hard surfaces, the formulation comprising:
   a glycol selected from the group consisting triethylene glycol (TEG), dipropylene glycol, propylene glycol and mixtures thereof;
   a quaternary ammonium salt; and
   a plurality of corrosion inhibitors comprising
      a first corrosion inhibitor that is selected from the group consisting of di-potassium phosphate, di-sodium phosphate, di-ammonium phosphate and mixtures thereof,
      a second corrosion inhibitor that is selected from the group consisting of mono-potassium phosphate, mono-sodium phosphate, mono-ammonium phosphates and mixtures thereof, and
      a third corrosion inhibitor selected from the group consisting of potassium nitrite, sodium nitrite, ammonium nitrite and mixtures thereof.

2. The formulation of claim 1 wherein the quaternary ammonium salt is an alkyl dimethyl benzyl ammonium saccharinate.

3. The formulation of claim 1 wherein the glycol is TEG.

4. The formulation of claim 1 wherein the first corrosion inhibitor is di-potassium phosphate and the second corrosion inhibitor is mono-potassium phosphate and the third corrosion inhibitor is potassium nitrite.

5. The formulation of claim 4 further comprising ethanol.

6. The formulation of claim 5 further comprising water.

7. The formulation of claim 6 further comprising at least one hydrocarbon propellant.

8. The formulation of claim 7 further comprising fragrance.

9. The formulation of claim 2 wherein the alkyl dimethyl benzyl ammonium saccharinate is selected from the group consisting of $C_{14}$, $C_{12}$ and $C_{16}$ dimethyl benzyl ammonium saccharinates.

10. The formulation of claim 2 wherein the alkyl dimethyl benzyl ammonium saccharinate comprises a mixture of $C_{14}$, $C_{12}$ and $C_{16}$ alkyl dimethyl benzyl ammonium saccharinates.

11. The formulation of claim 10 wherein the mixture of $C_{14}$, $C_{12}$ and $C_{16}$ alkyl dimethyl benzyl ammonium saccharinates consists essentially of about 50 wt % $C_{1-4}$ alkyl dimethyl benzyl ammonium saccharinate, about 40 wt % $C_{1-2}$ alkyl dimethyl benzyl ammonium saccharinate and about 10 wt % $C_{1-6}$ alkyl dimethyl benzyl ammonium saccharinate.

12. An aerosol formulation for sanitizing air, sanitizing soft surfaces, treating odors embedded in soft surfaces, and disinfecting hard surfaces, the formulation comprising:
from about 3 to about 10 wt % triethylene glycol;
from about 0.1 to about 1 wt % of at least one alkyl dimethyl benzyl ammonium saccharinate;
from about 10 to about 40 wt % water;
from about 30 to about 70 wt % of an alcohol; and
a plurality of corrosion inhibitors comprising
a first corrosion inhibitor that is selected from the group consisting of di-potassium phosphate, di-sodium phosphate, di-ammonium phosphate and mixtures thereof,
a second corrosion inhibitor that is selected from the group consisting of mono-potassium phosphate, mono-sodium phosphate, mono-ammonium phosphates and mixtures thereof, and
a third corrosion inhibitor selected from the group consisting of potassium nitrite, sodium nitrite, ammonium nitrite and mixtures thereof.

13. The formulation of claim 12 wherein the at least one alkyl dimethyl benzyl ammonium saccharinate is a mixture of C14, C12, and C16 alkyl dimethyl benzyl ammonium saccharinates consisting essentially of about 50 wt % C14 alkyl dimethyl benzyl ammonium saccharinate, about 40 wt % C12 alkyl dimethyl benzyl ammonium saccharinate and about 10 wt % C16 alkyl dimethyl benzyl ammonium saccharinate.

14. A method for sanitizing air, sanitizing soft surfaces, treating odors embedded in soft surfaces and disinfecting hard surfaces with a single formulation, the method comprising:
providing a formulation according to claim 1;
spraying the formulation in the air;
spraying the formulation on a soft surface; and
spraying the formulation on a hard surface.

15. The method of claim 14 further comprising:
allowing the formulation to absorb into the soft surface and make contact with a malodorant disposed within the soft surface;
allowing the composition to form agglomerations within the soft surface; and
allowing malodorants disposed in the soft surface to absorb into the agglomerations.

16. The method of claim 14 wherein the quaternary ammonium salt is an alkyl dimethyl benzyl ammonium saccharinate.

17. The method of claim 16 wherein the glycol is TEG.

18. The method of claim 14 wherein the first corrosion inhibitor is di-potassium phosphate and the second corrosion inhibitor is mono-potassium phosphate and the third corrosion inhibitor is potassium nitrite.

19. The method of claim 16 wherein the alkyl dimethyl benzyl ammonium saccharinate comprises a mixture of $C_{14}$, $C_{12}$ and $C_{16}$ alkyl dimethyl benzyl ammonium saccharinates.

20. The method of claim 19 wherein the mixture of $C_{14}$, $C_{12}$ and $C_{16}$ alkyl dimethyl benzyl ammonium saccharinates consists essentially of about 50 wt % $C_{1-4}$ alkyl dimethyl benzyl ammonium saccharinate, about 40 wt % $C_{1-2}$ alkyl dimethyl benzyl ammonium saccharinate and about 10 wt % $C_{1-6}$ alkyl dimethyl benzyl ammonium saccharinate.

21. A method for sanitizing air, sanitizing soft surfaces, treating odors embedded in soft surfaces and disinfecting hard surfaces with a single formulation, the method comprising:
providing an aerosol formulation comprising from about 4 to about 10 wt % triethylene glycol, from about 0.1 to about 1 wt % of at least one alkyl dimethyl benzyl ammonium saccharinate, from about 10 to about 40 wt % water, from about 30 to about 70 wt % of an alcohol; and a plurality of corrosion inhibitors including a first corrosion inhibitor that is selected from the group consisting of di-potassium phosphate, di-sodium phosphate, di-ammonium phosphate and mixtures thereof, a second corrosion inhibitor that is selected from the group consisting of mono-potassium phosphate, mono-sodium phosphate, mono-ammonium phosphates and mixtures thereof, and a third corrosion inhibitor selected from the group consisting of potassium nitrite, sodium nitrite, ammonium nitrite and mixtures thereof;
spraying the formulation in the air;
spraying the formulation on a soft surface;
allowing the composition to form agglomerations within the soft surface;
allowing malodorants disposed in the soft surface to absorb into the agglomerations; and
spraying the formulation on a hard surface.

22. An aerosol product for sanitizing air, sanitizing soft surfaces, treating odors embedded in soft surfaces, and disinfecting hard surfaces, the product comprising:
a pressurized aerosol vessel having an interior not susceptible to corrosion by a pressurized aqueous solution contained therein;
the pressurized aqueous solution comprising
a composition according to claim 1
water;
an alcohol; and
propellant.

23. The product of claim 22 wherein the vessel is made from aluminum.

24. The product of claim 22 wherein the vessel has an interior surface coated with a protective polymer.

* * * * *